United States Patent [19]

Sharkan

[11] Patent Number: 4,869,269

[45] Date of Patent: Sep. 26, 1989

[54] CONTRACEPTIVE DEVICE: MICRO-CONDOM

[76] Inventor: Arnold L. Sharkan, 9120-D Niles Center Rd., Skokie, Ill. 60076

[21] Appl. No.: 143,631

[22] Filed: Jan. 13, 1988

Related U.S. Application Data

[63] Continuation-in-part of Ser. No. 14,772, Feb. 13, 1987, abandoned.

[51] Int. Cl.$^4$ .............................................. A61F 13/00
[52] U.S. Cl. ..................................... 128/844; 604/349
[58] Field of Search ............................... 604/332–345, 604/349–353; 128/842, 844

[56] References Cited

U.S. PATENT DOCUMENTS

| | | | |
|---|---|---|---|
| 822,092 | 5/1906 | Woodruff | 604/352 |
| 2,305,453 | 12/1942 | Martos | 128/844 |
| 3,037,508 | 6/1962 | Friedman | 604/349 |
| 3,648,700 | 3/1972 | Warner | 128/294 |
| 3,677,225 | 7/1972 | Czirely | 128/132 |
| 3,878,847 | 4/1975 | Marsan | 128/283 |
| 3,951,141 | 4/1976 | Kopelowicz | 128/294 |
| 4,320,752 | 3/1982 | Comparetto | 128/132 R |
| 4,589,874 | 5/1986 | Riedel et al. | 604/349 |
| 4,638,790 | 1/1987 | Conway et al. | 128/844 |
| 4,640,688 | 2/1987 | Hauser | 604/352 |
| 4,731,064 | 3/1988 | Heyden | 604/352 |

FOREIGN PATENT DOCUMENTS

| | | | |
|---|---|---|---|
| 0096564 | 10/1922 | Switzerland | . |
| 1595711 | 3/1977 | United Kingdom | . |
| 1595711 | 8/1981 | United Kingdom | 604/349 |
| 86/00816 | 2/1986 | World Int. Prop. O. | . |

Primary Examiner—Jerome L. Kruter
Attorney, Agent, or Firm—Willian Brinks Olds Hofer Gilson & Lione

[57] ABSTRACT

A new and useful contraceptive-prophylactic condom is provided which, by means of a novel configuration and a medical grade adhesive, forms a leak-free seal with the tip (glans section) of the male sex organ. This invention eliminates the need for the roll-down hood present in a conventional contraceptive-prophylactic devices, providing increased user pleasure and reduced risk of unwanted pregnancy and venereal disease. Because the roll-down hood is eliminated, the breakage problem associated with conventional condoms can also be substantially solved without sacrificing user pleasure by manufacturing the condom of the invention from a thicker material.

5 Claims, 2 Drawing Sheets

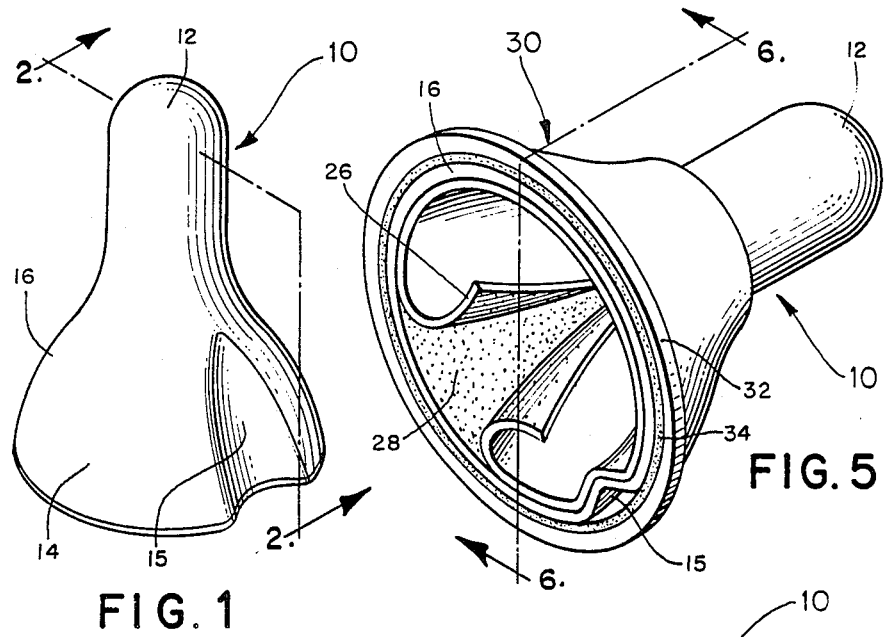
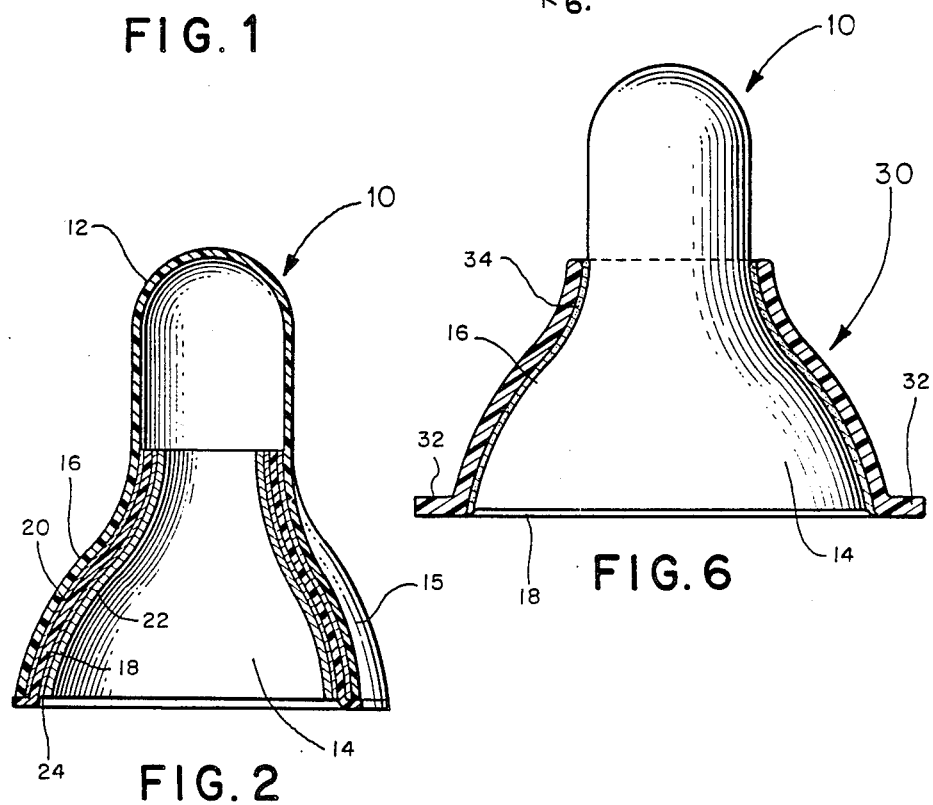

CONTRACEPTIVE DEVICE: MICRO-CONDOM

RELATED APPLICATIONS

This application is a continuation-in-part application of U.S. Ser. No. 07/014,772 filed Feb. 13, 1987, now abandoned.

FIELD OF THE INVENTION

This application relates to a new and useful contraceptive-prophylactic device which, by means of a novel configuration and a medical grade adhesive, adheres to the tip (glans section) of the male sex organ, eliminating the need for the roll-down hood present on conventional contraceptive-prophylactic devices, providing increased user pleasure and reduced risk of unwanted pregnancy and venereal disease.

BACKGROUND OF THE INVENTION

Contraceptive-prophylactic devices, otherwise known as condoms, are well known in the art for their role in preventing unwanted pregnancy and preventing or reducing the spread of various venereal diseases. Conventional condoms cover both the penile head and the penile shaft and utilize a roll-down hood for installation onto the penile shaft. A disadvantage of conventional condoms is that they can slip off the penis during usage allowing leakage of semen into the vaginal passage. Another disadvantage is that these condoms can break during usage. The breakage problem can be eliminated or reduced substantially by manufacturing the condom from a thicker material but this causes reduction in user pleasure.

Attempts have been made to solve the leakage problem by utilizing an adhesive material to secure the hood of the condom to the penile shaft. U.S. Pat. No. 4,638,790, for instance, discloses a condom in which the hood, initially in a rolled-up configuration, has an outer member which releases adhesive onto the inner surface of the condom as the hood is unrolled, the outer member being removed after the condom is in place. A projecting head is provided on the outer member for grasping the outer member to facilitate its removal. Lubricant may be present between the inner and outer members to further facilitate removal of the outer member and to facilitate use of the condom during intercourse. This condom solves the problem of leakage but does not eliminate the breakage problem, or the problem of reduced user pleasure if the thickness is increased to prevent breakage.

U.S. Pat. No. 3,677,225 discloses an adhesive-supported condom which covers only the tip of the male sex organ and does not include a roll-down hood. This device is targeted toward increased user pleasure but is not designed according to the shape of the tip of the male sex organ. The symmetrical flange-like design of this device would not only cause leakage problems but may dislodge completely during use because the area of attachment between the condom and the male sex organ is insufficient to allow the condom to become securely sealed to the tip of the sex organ.

SUMMARY OF THE INVENTION

The primary object of the present invention is to provide a contraceptive condom which increases user pleasure and at the same time solves the leakage and breakage problems associated with contraceptive condoms of the prior art.

A second object of the invention is to provide a contraceptive condom which is easy to handle, to install, and to remove.

The present invention employs a specially-formed, sealed receptacle manufactured from natural latex, animal membrane, or similar material to act as a barrier to avoid the exchange of body fluids during sexual intercourse. More particularly, the contraceptive condom of the present invention is uniquely formed to configure to the shape of the tip (glans penis) of the male sex organ. The condom of the invention has a relatively narrow elongated portion closed on one end for collecting seminal fluid and a wider, generally frustro-conical portion which fits over and adheres to the glans penis. An indenture in the underside of the generally frustro-conical portion is provided which corresponds to the indenture in the underside of the glans penis. The condom is held in place and forms a leak-free seal with the glans penis by means of a pressure-sensitive medical grade adhesive.

The use of an adhesive combined with the special shape of the condom of the invention allows elimination of the roll-down hood portion which is primarily responsible for the diminished pleasure of the conventional condoms of the prior art. The condom of the invention covers only the glans penis and does not cover the "corona" (i.e. the ridge surrounding the glans penis) or the frenulum (i.e. the underside, where the glans meets the foreskin), which are the most sensitive part of the male sex organ. The special configuration combined with the adhesive causes formation of a leak-free seal between the condom and the male sex organ, a feature previously made possible only with the use of the roll-down hood.

Because the condom of the invention does not cover the sensitive corona or frenulum areas of the penis, the condom can be made as thick as is necessary to prevent breakage without causing reduction in user pleasure. For instance, the condom of the invention can be two to three times as thick as conventional condoms of the prior art.

The pressure-sensitive medical adhesive is distributed approximately uniformly around the inner surface of the generally frustro-conical portion and preferably covers the entire area of contact between the condom and the glans penis. The adhesive may be imparted to the inner surface of the condom by any commercially feasible method such as by spraying or through the use of a double adhesive coated medical tape or a supported or unsupported medical grade adhesive transfer film.

In a preferred embodiment, the condom of the invention may additionally comprise a removable handling means which aids in the installation of the condom.

The foregoing and other objects and advantages of the invention are explained in greater detail in the following detailed description of the preferred embodiments made with reference to the accompanying Figures.

BRIEF DESCRIPTION OF THE FIGURES

FIG. 1 is an upper perspective view of a contraceptive condom of the invention.

FIG. 2 is a cross-sectional view of a contraceptive condom of the invention in which adhesion to the glans penis is obtained through use of a double adhesive coated faced pressure sensitive medical tape initially covered with a removable liner.

FIG. 5 shows a lower perspective view of a condom of the invention which utilizes a removable exterior handle to facilitate installation.

FIG. 6 is a side view of the condom of FIG. 5 showing the exterior handle in cross section.

DETAILED DESCRIPTION OF THE FIGURES

Figure 3:
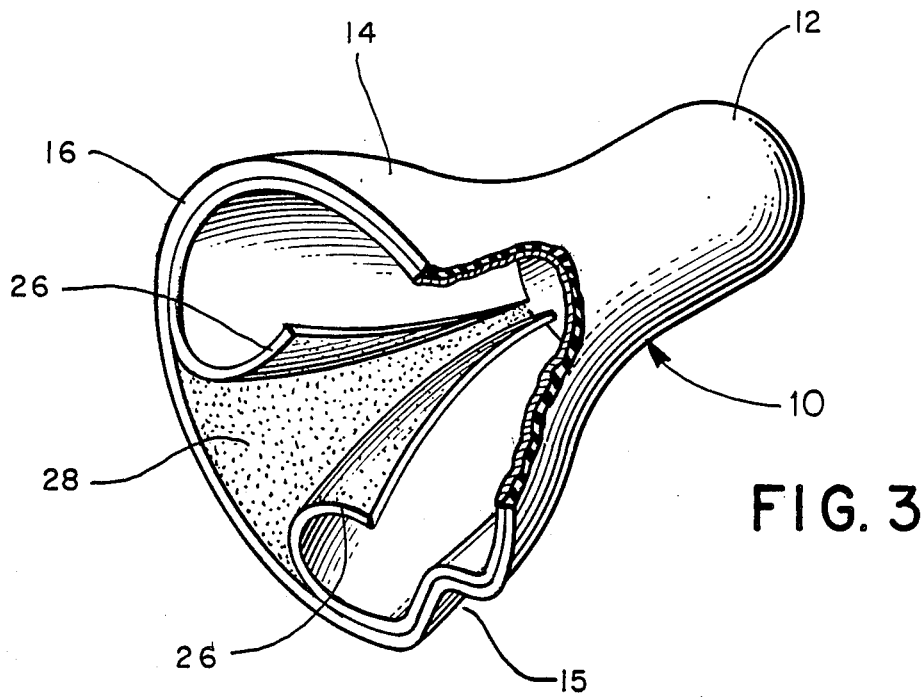
FIG. 3 is a lower perspective view of an alternative embodiment of the invention in which adhesion is obtained through use of an unsupported pressure sensitive adhesive transfer film, the transfer film being removed when the condom is installed.

Referring to FIGS. 1 and 2, a contraceptive prophylactic condom generally designated as 10 comprises an elongated, close-ended seminal receptacle 12 and a wider, open ended generally frustro-conical portion 14. An indenture 15 is provided in the frustro-conical portion 14 to correspond approximately the indenture in the underside of the tip (glans penis) of the male sex organ. The condom 10 includes an outer layer 16 of approximately uniform thickness and formed from a natural latex, animal membrane, or other suitable material. The thickness of the outer layer 16 is preferably between about 0.003 inches and about 0.009 inches, and most preferably about 0.007 inches. This thickness may vary somewhat depending upon the type of material used in the outer layer 16 but should be of sufficient to prevent breakage or tearing of the condom during installation and use of the condom.

The generally frustro-conical region 14 of the condom 10 is covered on the inside by a double adhesive coated medical tape 18 which is permanently bonded to the outer layer 16 by means of a first adhesive layer 20 and which is temporarily bonded to a removable liner 22 by means of a second adhesive layer 24. The double adhesive coated medical tape 18 is of a pressure sensitive variety, such as #1512 1.5 mil (0.038 mm) polyethylene double adhesive coated tape manufactured by 3M Medical Products Division, St. Paul, Minn. 55144.

The removable liner 22 both protects the adhesive layer 24 and provides structural support for the condom 10. Prior to installation of the condom 10, the liner 22 is peeled away so as to expose the adhesive layer 24. As the condom 10 is pressed into place, the adhesive layer 24 forms a strong, leak-free seal with the tip (glans penis) of the male sex organ.

FIG. 3 shows an alternative embodiment of the contraceptive condom 10 of FIG. 1 in which the double adhesive coated medical adhesive tape 18 is eliminated and replaced instead with an unsupported medical grade adhesive transfer film 26 which imparts a single adhesive layer 28 onto the inner surface of the outer layer 16. Prior to installation of the condom 10, the transfer film 26 is removed, exposing the adhesive layer 28 for direct contact with the glans penis to form a strong, leak-free seal. Examples of commercially available medical grade adhesive transfer films suitable for this purpose are Fitchburg 545, 591, 594, and 597 free films coated onto a thermoformable polyester liner.

Figure 4:
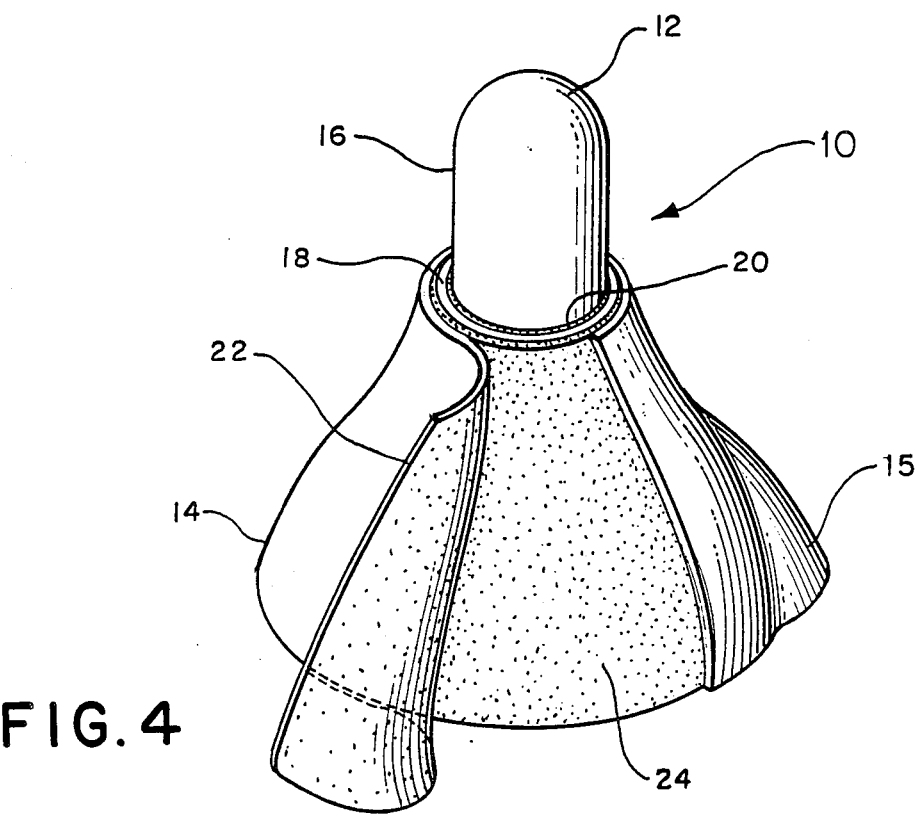
FIG. 4 shows a perspective view of the condom of FIG. 2 turned inside out to facilitate removal of the inner liner 22 prior to installation.

In FIG. 4 the contraceptive condom 10 of FIG. 2 is turned inside out in order to facilitate easy removal of the inner liner 22 prior to installation of the condom 10. The reason for turning the condom 10 inside out is so that the pulling action required to peel the inner liner 22 away from the adhesive layer 24 will not cause the condom 10 to fold inward causing the generally frustro-conical portion 14 to collapse and further causing different portions of the adhesive layer 24 to overlap and bond together. Alternatively, and perhaps move conveniently, the condom 10 may be turned only partially inside out to take the shape of a hat such that the liner 22 is facing outward while the elongated receptacle 12 is still turned inward. By turning only the generally frustro-conical portion 14 inside out, less manipulation of the condom is required to install the condom after the liner 22 has been removed.

It is understood that, while the foregoing description of FIG. 4 is made only with reference to the embodiment shown in FIG. 2, the condom 10 shown in FIG. 3 could likewise be turned totally or partially inside out to allow easier removal of the adhesive transfer film 26.

It is further understood that the indentured adhesive condom 10 of the invention is not limited to the adhesive means shown in FIGS. 1 and 2. In alternative embodiments not shown, for instance, adhesive can be sprayed, squirted, or extruded onto the inner surface of the frustro-conical portion 14 of the outer layer 16 and a polyester protective liner can be inserted atop the adhesive layer prior to use of the condom 10. A suitable adhesive for spraying is Monsanto Gelva Acrylic Water-Based Medical Grade Adhesive 2222. A suitable apparatus for spraying is the Nordson Airless Spray System, or a similar apparatus. Suitable adhesives for squirting or extruding include hot melt adhesives supplied by National Starch and Chemical Co. A suitable apparatus for applying a hot melt adhesive is the #2300 Hot Melt System available from Nordson Corp.

A preferred embodiment of the condom 10, shown in FIG. 5, includes an exterior handle 30 with a handling rim 32 to facilitate installation. Preferably, the handle 30 is made of a layer of plastic material between 0.015 and 0.020 inches thick. The handle 30 is removably laminated around the exterior of the frustro-conical portion 14 by means of a bonding layer 34 which can be a mild adhesive or a gel or similar lubricating material. By grasping the handle at the rim 32, the condom 10 can be installed without extensive direct handling which can cause the condom 10 to collapse causing the inner adhesive surfaces to stick together. After the condom has been adhesively secured to the glans penis, the handle 30 can be removed from the condom 10 by pulling the rim 32 forward. Where a lubricating gel is used as the bonding layer 34 any gel which remains on the outer surface of the frustro-conical portion 14 after removal of the handle 10 will act as a lubricant during intercourse.

An additional advantage of utilizing a handle 30 is that it provides structural support for the condom 10 before and during installation. This obviates the need to turn the condom 10 inside out in order to remove the inner liner 22 of FIG. 2 or the adhesive transfer film 26 of FIG. 3. As shown in FIG. 5, for example, the adhesive transfer film 26 can now be removed from the inside of the condom 10 without causing the condom to collapse.

Because the condom of the invention covers only the tip of the male sex organ and does not utilize a roll-down hood, the problem of diminished user pleasure is eliminated and the condom can be made as thick as is necessary to eliminate breakage. Because the condom of the invention is specially formed with an indenture for fitting onto the tip of the male sex organ, and because a pressure sensitive adhesive is used to hold the condom in place and form a complete seal with the tip of the male sex organ, the leakage problems associated with the condoms of the prior art are eliminated.

While the embodiments described herein are at present considered to be preferred, it is understood that various modifications and improvements may be made therein without departing from the invention. The scope of the invention is indicated in the appended claims and all changes that come within the meaning and range of equivalency of the claims are intended to be embraced therein.

I claim:

1. A contraceptive prophylactic condom comprising a seminal receptacle having an open end and a closed end, a wider generally frustro-conical portion adjacent to and extending outwardly from the seminal receptacle corresponding approximately in size and shape to the glans penis of the male sex organ and having an indenture formed of continuous surface corresponding approximately to the indenture in the underside of the glans penis of the male sex organ, and adhesive means on an inner surface of the generally frustro-conical portion for sealing the condom to the tip of the male sex organ.

2. The condom of claim 1 wherein the adhesive means comprises a double adhesive coated medical tape having a first adhesive layer which permanently secures the tape to the inner surface of the generally frustro-conical portion, a second adhesive layer for securing the condom to the glans penis of the male sex organ, and a removable liner for covering the second adhesive layer prior to use of the condom.

3. The condom of claim 1 wherein the adhesive means comprises a medical grade adhesive transfer film for imparting a single adhesive layer onto the inner surface of the generally frustro-conical portion for securing the condom to the glans penis of the male sex organ, the transfer film removably secured to the inner surface of the generally frustro-conical portion and covering the adhesive layer prior to use of the condom.

4. The condom of claim 1 wherein the adhesive means comprises an adhesive layer imparted by spraying a medical adhesive onto the inner surface of the generally frustro-conical portion of the condom.

5. The condom of claim 1 further comprising a handle removably secured to an exterior surface of the generally frustro-conical portion of the condom, the handle having a rim to facilitate installation of the condom and removal of the handle after installation of the condom.

* * * * *